(12) United States Patent
Cheng

(10) Patent No.: US 9,908,645 B2
(45) Date of Patent: Mar. 6, 2018

(54) PORTABLE CONTAINER AND METHOD OF MANUFACTURING THE SAME

(75) Inventor: Chin-Chung Cheng, Miaoli (TW)

(73) Assignee: HARMONY BIOSCIENCES, INC., San Gabriel, CA (US)

( * ) Notice: Subject to any disclaimer, the term of this patent is extended or adjusted under 35 U.S.C. 154(b) by 848 days.

(21) Appl. No.: 13/457,292

(22) Filed: Apr. 26, 2012

(65) Prior Publication Data

US 2013/0287472 A1    Oct. 31, 2013

(51) Int. Cl.
| | |
|---|---|
| *B65D 3/00* | (2006.01) |
| *B65B 3/00* | (2006.01) |
| *B65B 31/00* | (2006.01) |
| *B65D 1/09* | (2006.01) |
| *B65D 81/20* | (2006.01) |
| *A45D 34/04* | (2006.01) |
| *A45D 40/00* | (2006.01) |
| *A61F 13/40* | (2006.01) |
| *A61J 1/06* | (2006.01) |

(52) U.S. Cl.
CPC .............. *B65B 3/003* (2013.01); *A45D 34/04* (2013.01); *A45D 40/0087* (2013.01); *B65B 31/00* (2013.01); *B65D 1/09* (2013.01); *B65D 81/20* (2013.01); *A45D 2200/1018* (2013.01); *A45D 2200/1045* (2013.01); *A61J 1/065* (2013.01); *A61M 35/006* (2013.01)

(58) Field of Classification Search
CPC ...... B65D 81/2015; B65D 1/09; B65D 3/003; A61J 1/06; A61J 1/065; A61M 35/006
USPC .......... 401/123, 132–135; 220/266; 604/1–3; 215/250, 253, 256; 53/405
See application file for complete search history.

(56) References Cited

U.S. PATENT DOCUMENTS

| | | | | | |
|---|---|---|---|---|---|
| 2,198,752 | A | * | 4/1940 | Barr ................................ | 53/405 |
| 4,492,305 | A | * | 1/1985 | Avery ........................... | 401/132 |
| 4,707,450 | A | * | 11/1987 | Nason .................... | A61B 10/02 206/438 |
| 5,221,311 | A | * | 6/1993 | Rising ..................... | B01L 3/569 215/47 |
| 5,511,654 | A | * | 4/1996 | de la Rocha .......... | A45D 40/24 206/15.3 |
| 5,690,958 | A | * | 11/1997 | McGrath ............. | A61M 35/006 424/405 |
| 2004/0197730 | A1 | * | 10/2004 | Rowe ....................... | A61C 5/60 433/80 |
| 2006/0228158 | A1 | * | 10/2006 | Levine ............... | A61M 35/006 401/130 |

* cited by examiner

Primary Examiner — Jennifer C Chiang
Assistant Examiner — Bradley Oliver
(74) Attorney, Agent, or Firm — Lewis Roca Rothgerber Christie LLP

(57) ABSTRACT

A portable cosmetic container is disclosed. The portable cosmetic container includes a tube that has a receiving space with an opening at one end, and a crease is located at a bottom portion of the receiving space, so that a user can easily break the tube from the crease to form the opening of the receiving space. Substance is partially filled in the receiving space, and air therein is extracted to form a negative pressure status. It is advantageous that when a user breaks the tube from the crease, the substance will not randomly spray out since the air pressure moves towards the opening to keep the substance in the receiving space.

14 Claims, 10 Drawing Sheets

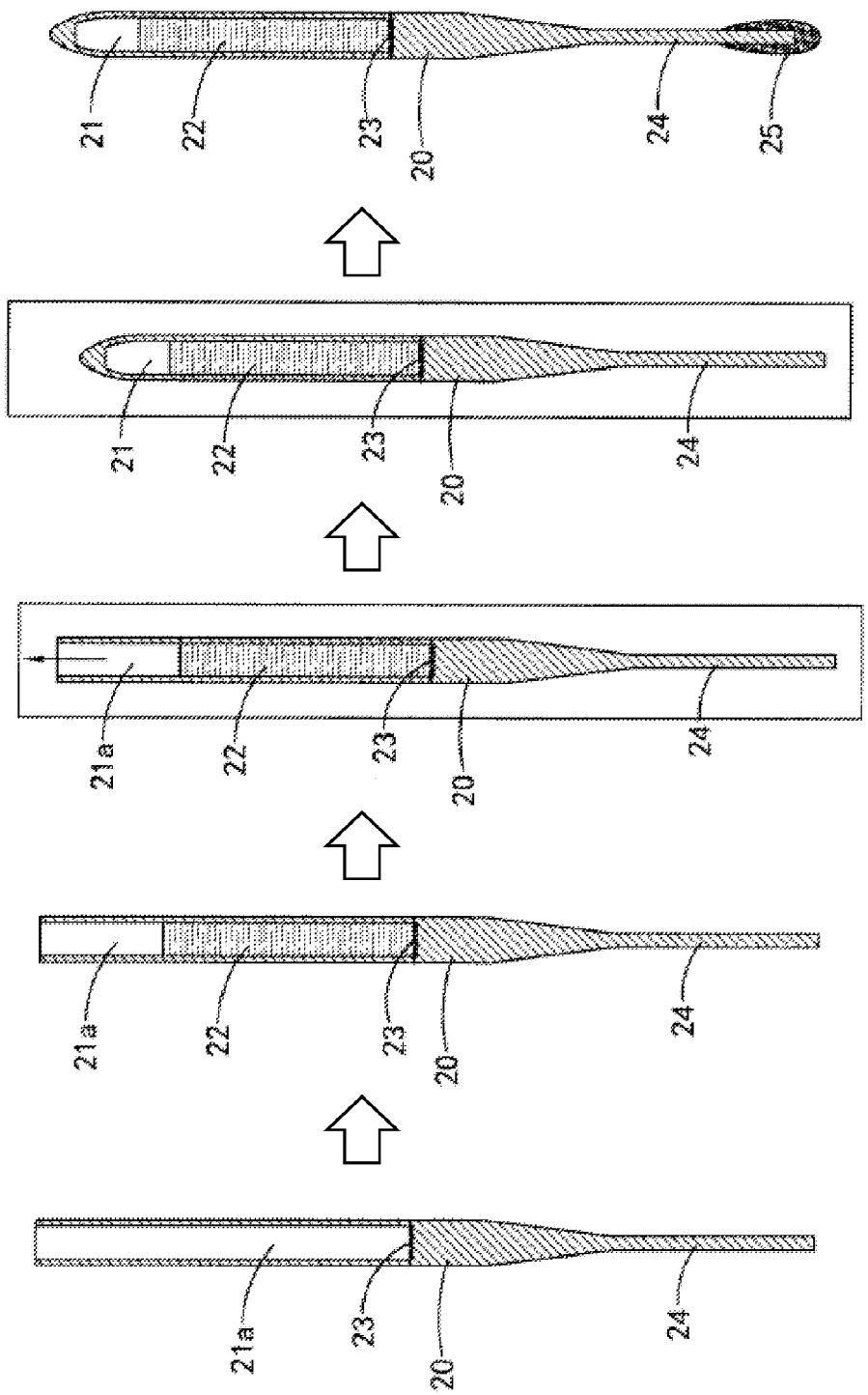

PORTABLE CONTAINER AND METHOD OF MANUFACTURING THE SAME

FIELD OF THE INVENTION

The present invention relates to a container, and more particularly to a portable cosmetic container that can safely secure the substance therein to avoid spraying when a user opens the container.

BACKGROUND OF THE INVENTION

As can be seen in FIG. 1, a conventional cosmetic container includes a tubing unit 10 having a receiving chamber 11, and one end of the tubing unit 10 is sealed when the receiving chamber 11 is filled with substance 12, so that the receiving chamber 11 is in a sealed status including the substance 12 along with an air space 13. Also, as shown in FIGS. 2 and 2a, a cotton or a brush 14 can be attached to the sealed end of the tubing unit 10 to form a cotton swab, which can be moistened by the substance 12 when inserted into the receiving chamber 11.

However, once the tubing unit 10 is sealed, the air in the receiving chamber 11 is compressed, so the air pressure of the air space 13 is greater than one atmospheric pressure when the sealing process is completed. The user can break the tubing unit 10 from a crease 15 when the user would like to use the substance 12 in the receiving chamber 11. Since the pressure in the air space 13 is greater than one atmospheric pressure, when the tubing unit 10 is broken from the crease 15, the pressure in the air space 13 releases to reach a steady state with an environment outside. Meanwhile, the pressure in the air space 13 that is greater than one atmospheric pressure may cause the substance 12 to randomly spray out, and cause some waste of the substance 12 as well.

U.S. Pat. No. 5,515,991 to Heitland discloses a cosmetics container that has a receiving segment with a planar bottom and which is sealable by an air-hermetic main cover as shown in FIG. 3 In Heitland, there are two sealing surfaces: a first sealing surface (115) is between the intermediate cover and the horizontal step in the receiving segment, and a second sealing (114) surface is between the intermediate cover and the main cover resting on the intermediate cover. Thus, materials can be stored behind two sealing surfaces inside the receiving segment. However, the material might spray out as shown in FIG. 2a if the air pressure is greater than one atmospheric pressure when the material is sealed.

U.S. Pat. Pub. No. 2011/0299911 discloses a cosmetic container having a container main body, a moving part, a middle cylinder part, and an application body. The container main body houses a cosmetic. When the moving part is positioned at a first stopping position, the closing part of the discharge cylinder closes the insertion hole of the middle cylinder part and seals the cosmetic. When the moving part is moved from the first stopping position to a second stopping position separated in the axial direction, the discharge cylinder protrudes by a predetermined length from the end face of the insertion hole and exposes the slit of the discharge cylinder. Thus, a user can visually confirm the condition that the cosmetic can flow out to the outside through the slits, the inside of the discharge cylinder, and the opening part. However, similar to Heitland, the cosmetic may randomly spray out if the air pressure is greater than one atmospheric pressure when the cosmetic is sealed.

Therefore, there remains a need for a new and improved structure of the cosmetic container that can overcome the problems stated above.

SUMMARY OF THE INVENTION

The main object of the present invention is to provide a portable cosmetic container, and when a user opens the container, substance in the container would not spray out.

In one aspect, the portable cosmetic container may include a tube that has a sealed receiving space inside, and the receiving space has substance that partially fills the receiving space, so that there remains an air space whose air pressure is less than one atmosphere pressure after the air is being extracted, namely a negative pressure status. A crease is formed at one end of the receiving space of the tube, so the tube can be easily broken from the crease to form an opening.

In one embodiment, the receiving space in the tube has an open end, and a bottom portion of the receiving space has a crease, so that the tube can be broken from the crease to form an opening from the bottom of the receiving space. The substance can be liquid, paste or powder in the receiving space. The negative pressure is formed when the air is extracted from the receiving space. The opening of the receiving space can be sealed to form a sealed receiving space in which the substance partially fills the receiving space, and the air pressure in the receiving space is still less than one atmosphere.

Therefore, the substance can be sealed in the receiving space, and when the user breaks the tube from the crease, the substance can be poured out easily. Namely, the substance can be safely kept in the receiving space until the user breaks the tube, so it is convenient for the user to carry without concern that the substance may unexpectedly come out. More importantly, when the tube is broken at the crease, the negative pressure (outside pressure is higher than the pressure in the receiving space) in the receiving space will keep the substance in the receiving space until the pressure reaches a steady state, so that the substance in the present invention will not randomly spray out when the tube is broken by the user.

BRIEF DESCRIPTION OF THE DRAWINGS

FIG. 9 illustrates a schematic view of the process flow in FIG. 8.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

Figure 1:
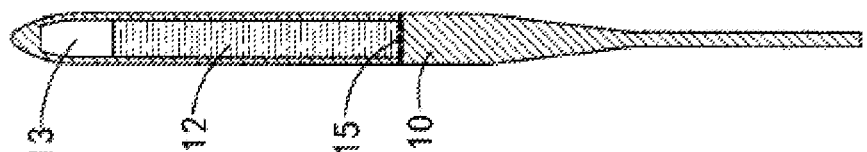
FIG. 1 illustrates a schematic view of a process flow to manufacture a conventional portable cosmetic container.
Figure 1:
Figure 1:
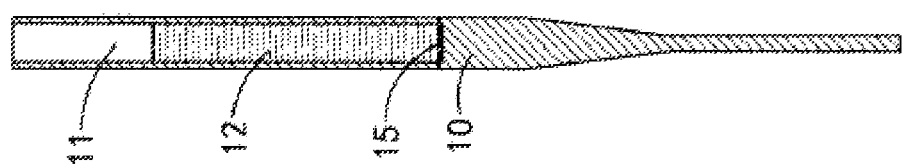
Figure 1:
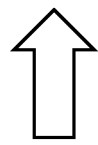
Figure 1:
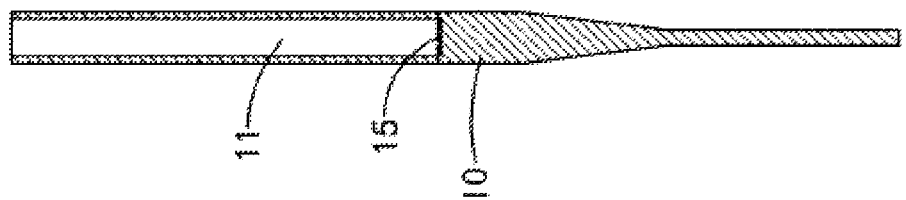
Figure 2:
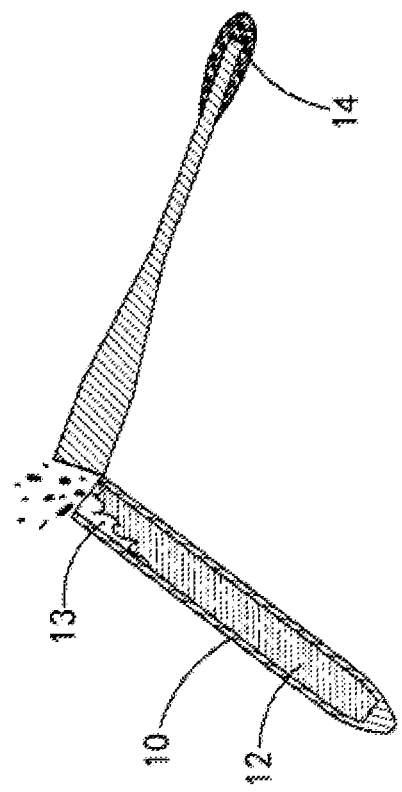
FIG. 2 illustrates a conventional structure of a cosmetic container including a cotton swab.
Figure 2A:
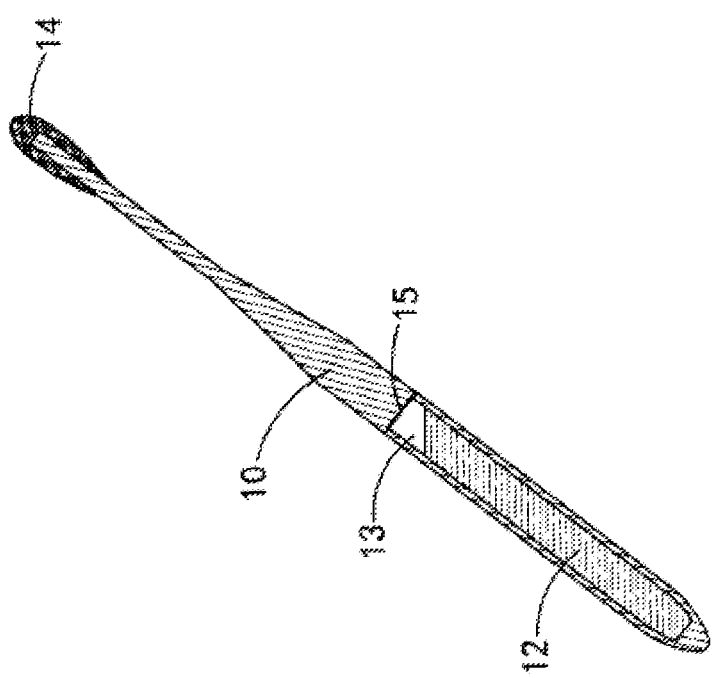
Figure 3:
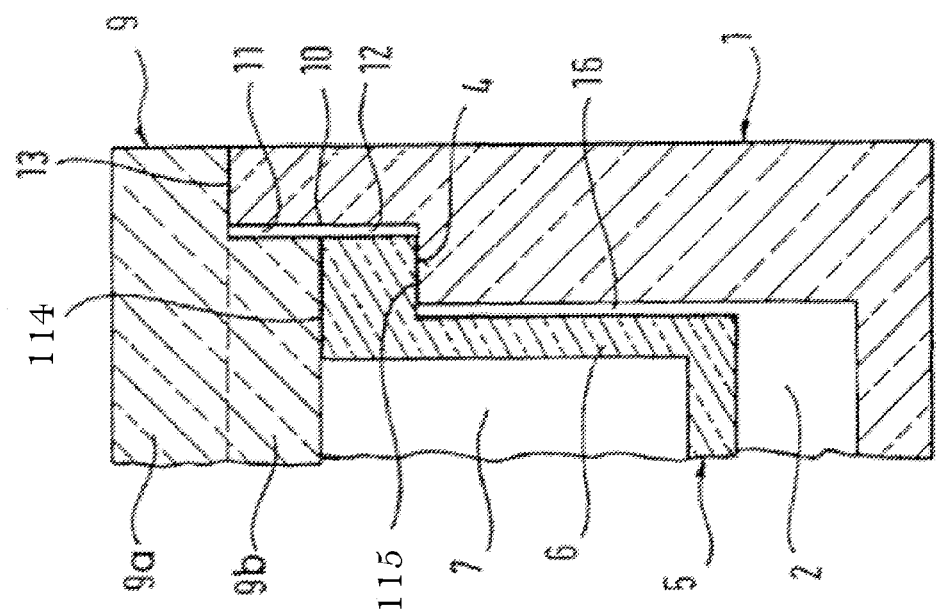
FIG. 3 illustrates prior art related to a cosmetic container having two sealing surfaces.
Figure 4A:
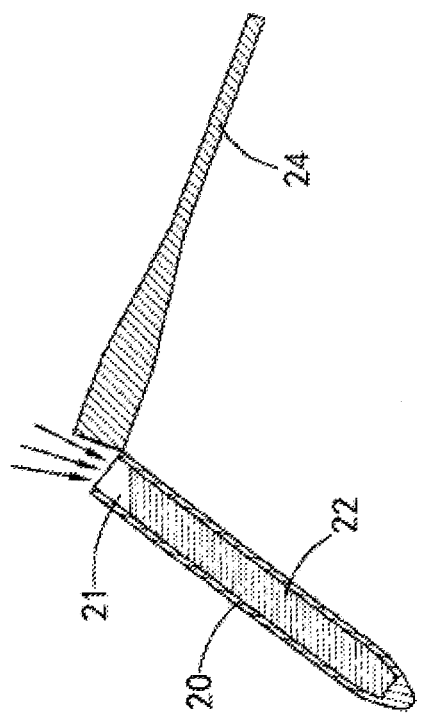
FIGS. 4 and 4a illustrate a schematic structural view of an embodiment of the present invention.
Figure 4:
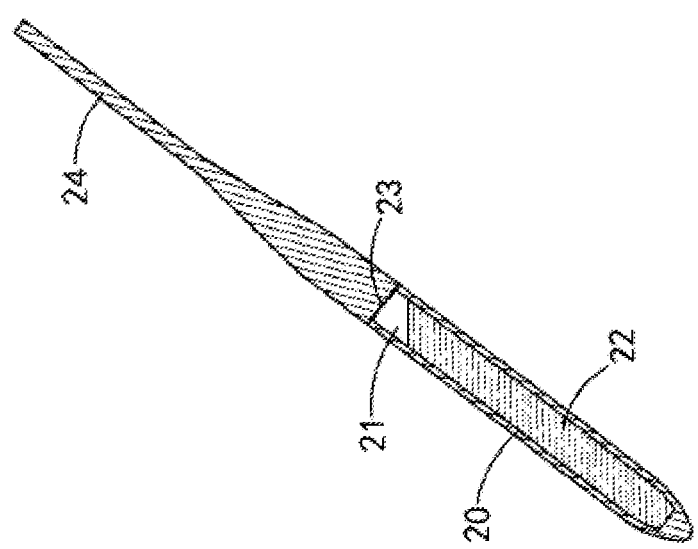

Referring to FIGS. 4 and 4a, a portable cosmetic container includes a tube 20 having a receiving space 21 that is sealed inside the tube 20. The receiving space has substance 22 therein, but the substance 22 does not fill the entire receiving space 21, and a small air space exists in the receiving space 21. In one embodiment, the status of the substance 22 can be liquid, paste or powder, and the substance 22 can be medicine or cosmetics. Furthermore, one end of the receiving space 21 of the tube 20 has a crease 23, which can be a circular groove with a thinner wall so that the user can easily break the crease 23 to reach the substance 22 in the receiving space 21. Furthermore, an extended end 24 is connected to the tube 20 at the crease 23, and the extended end 24 is tapered and solid. It is noted that air pressure in the air space of the receiving space 21 is actually "negative," meaning that the air pressure is lower than one atmospheric pressure, so that when the user breaks the tube 20 from the crease 23, the substance 22 will be safely held in the receiving space to avoid spraying out due to the pressure change.

After the tube 20 is sealed, the substance 22 is retained in the receiving space 21, so the tube 20 is portable without the concern of leaking. Also, it is convenient for the user to break the tube 20 from the crease 23 to pour the substance 22 out. More importantly, as stated above, when the user breaks the tube 20 from the crease 23, the air outside the tube 20 will keep the substance 22 in the receiving space 21 because the air pressure outside is greater than that in the receiving space. Namely, the receiving space 21 has a "negative pressure," so that the air outside the tube 20 moves towards the direction of the opening of the tube 20 to prevent the substance 22 from suddenly spraying out.

Figure 5A:
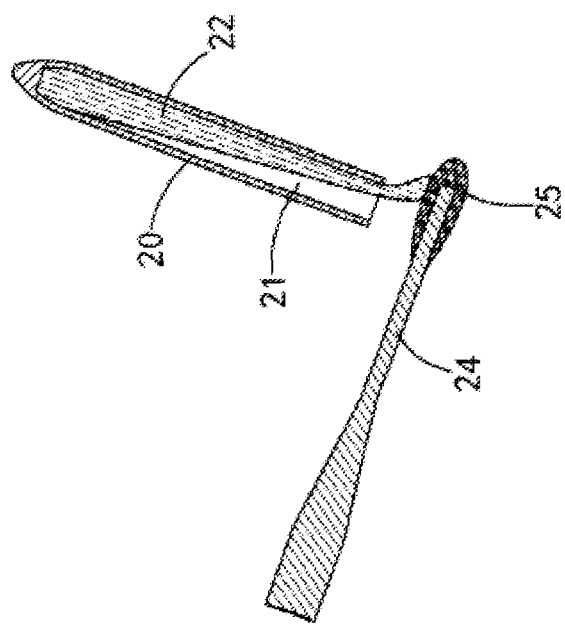
FIGS. 5 and 5a to 5c illustrate a structure of another embodiment of the present invention.
Figure 5:
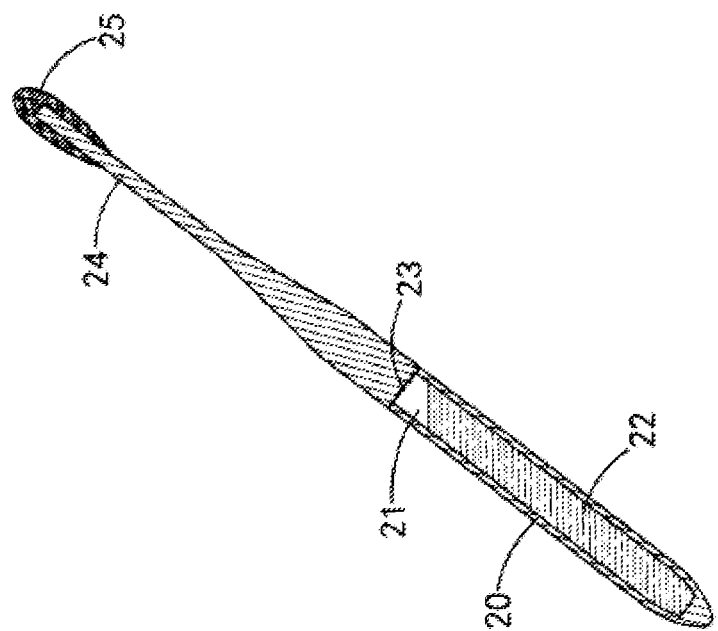

As illustrated in FIGS. 5 and 5a, a cotton 25 is attached to the tapered extended end 24 of the tube 20, which can be used as a cotton swab. When the user breaks the tube 20 from the crease 23 and waits until the pressure reaches a steady state, the user can tilt the tube 20 to pour the substance 22 out, or even squeeze the substance 22 out by squeezing the tube 20. The extended end 24 along with the cotton 25 can be disposed at the opening of the tube 20 to receive the substance 22, and used as a cosmetic or medical cotton swab.

Figure 5C:
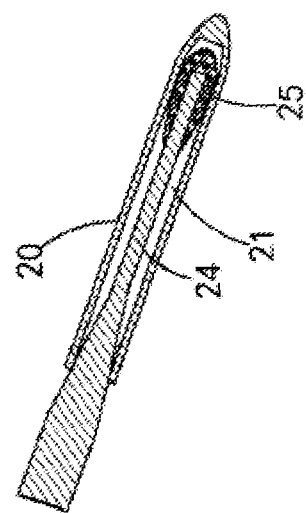
Figure 5B:
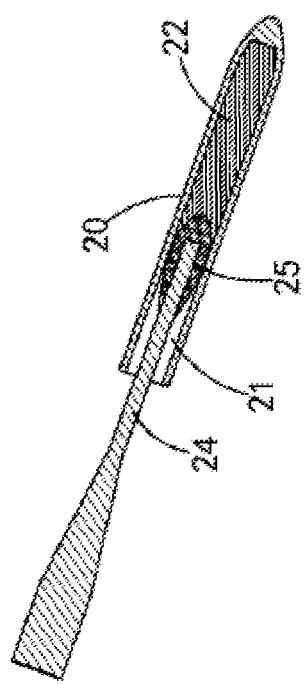

In another embodiment shown in FIGS. 5b and 5c, the extended end 24 with the cotton 25 can be directly inserted into the receiving space 21, so that the cotton 25 can be moistened with the substance 22. Also, the user can put the extended end 24 (with cotton 25) in the receiving space 21 after using it to seal the opening of the tube 20 to further reduce contamination.

Figure 6:
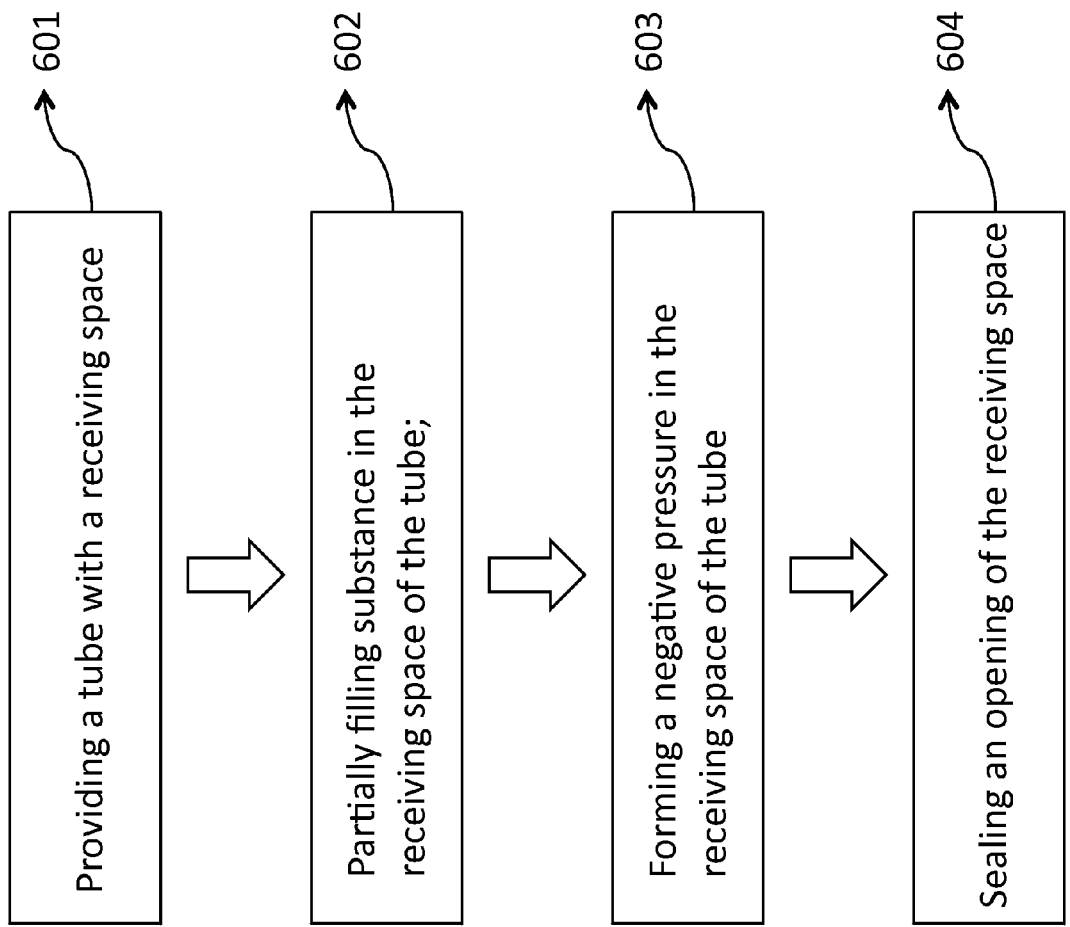
FIG. 6 illustrates a process flow to manufacture a portable cosmetic container according to an embodiment of the present invention.
Figure 7:
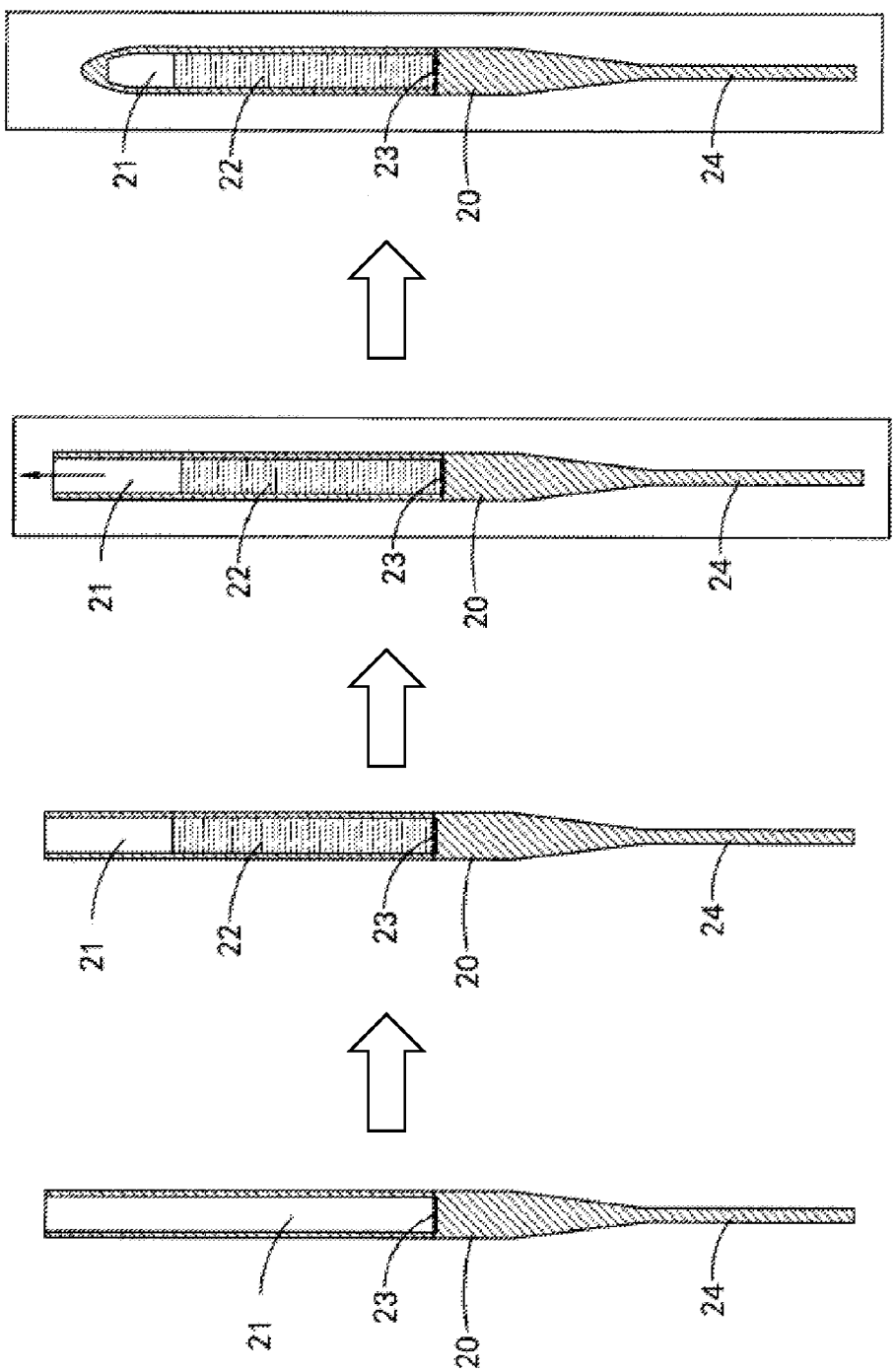
FIG. 7 illustrates a schematic view of the process flow in FIG. 6.

In another aspect as shown in FIGS. 6 and 7, a method for manufacturing a portable cosmetic container includes steps of providing a tube with a receiving space 601; partially filling substance in the receiving space of the tube 602; forming a negative pressure in the receiving space of the tube 603 and sealing an opening of the receiving space 604. In one embodiment, the step of providing a tube may include steps of providing a receiving space 21 inside the tube 20, and forming a crease 23 at a bottom portion of the receiving space 21, so that the tube 20 can be broken easily from the crease 23 to form an opening at the bottom portion of the receiving space 21. In a further embodiment, the step of forming a negative pressure 603 may include a step of extracting air from the receiving space 21, so that air pressure therein is lower than one atmospheric pressure. It is noted that when the opening of the receiving space 21 is sealed, the substance 22 does not fill the entire receiving space 21, and the negative pressure remains in the receiving space 21.

It is noted that even though the air pressure may increase when the opening of the receiving space 21 is sealed in step 604, the air pressure can still remain negative if more air has been extracted in step 603. Thus, when the user breaks the portable cosmetic container from the crease 23, the substance 22 will be kept inside the receiving space 21 to prevent the substance 22 from spraying out therefrom.

Figure 8:
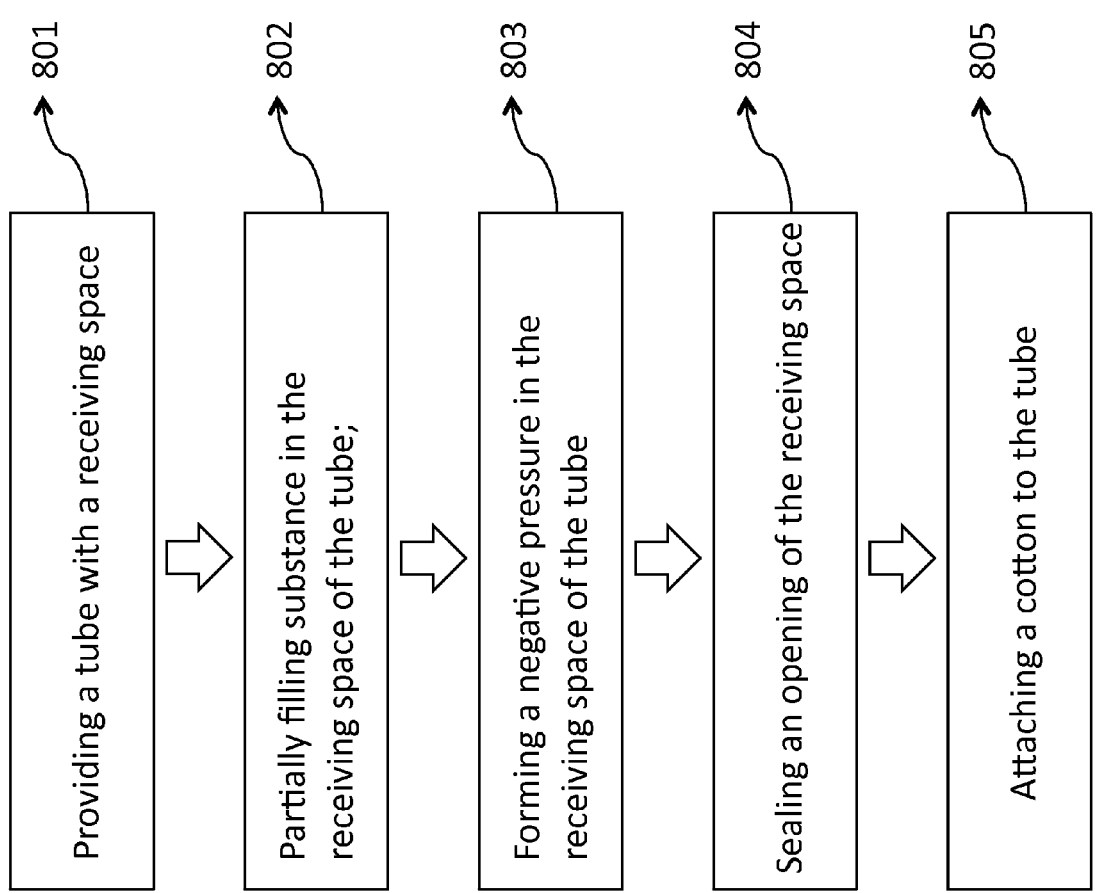
FIG. 8 illustrates a process flow of another embodiment to manufacture a portable cosmetic container of the present invention.

Referring to FIGS. 8 and 9 for another embodiment, a method for manufacturing a cosmetic container includes steps of providing a tube with a receiving space 801; partially filling substance in the receiving space of the tube 802; forming a negative pressure in the receiving space of the tube 803; sealing an opening of the receiving space 804; and attaching a cotton to the tube 805. As stated above, the tube 20 has the tapered and solid extended end 24 with a smaller diameter than the tube 20, and the extended end 24 is located at an opposite side of receiving space 21. A cotton 25 can be attached to the tapered extended end, so that the extended end 24 along with the cotton 25 can be used as a cotton swab for the portable cosmetic container according to this embodiment of the present invention.

The substance 22 in the present invention may include, but is not limited to, liquid medicine used for wounds in a family, such as hydrogen peroxide solution, merbromin solution, acrinol solution, methylrosaniline chloride solution, and providone solution. The substance 22 can also be maintenance cosmetics such as cleansing water, nail polish, and phytoncide.

In a further embodiment, the substance 22 can be chemicals, such as casein glue, urea formaldehyde glue, phenol formaldehyde glue, formaldehyde resin glue, acid-vinyl acetate rubber, and nitrocellulose glue. In still further embodiment, the substance 22 can be powder drugs or cosmetics, such as sulfa drug having anti-bacterial properties or other appropriate powder drugs.

Having described the invention by the description and illustrations above, it should be understood that these are exemplary of the invention and are not to be considered as limiting. Accordingly, the invention is not to be considered as limited by the foregoing description, but includes any equivalent.

What is claimed is:

1. A method of manufacturing a portable container, the method comprising:
   providing a tube with a receiving space;
   forming a crease at a bottom portion of the receiving space such that, when the tube is broken at the crease, a first opening is formed at a first end of the tube;
   partially filling a substance in the receiving space of the tube at a second opening at a second end of the tube opposite the first end thereof;
   forming a negative pressure in the receiving space of the tube after the partially filling the substance in the receiving space; and
   sealing the second opening of the receiving space after the forming the negative pressure in the receiving space.

2. The method of manufacturing the portable container of claim 1, wherein the forming the negative pressure comprises extracting air from the receiving space such that air pressure therein is less than one atmospheric pressure.

3. The method of manufacturing the portable container of claim 1, further comprising:
   providing a tapered, solid extended end extending from the first end of the tube adjacent the crease; and
   attaching cotton to the tapered, extended end.

4. The method of manufacturing the portable container of claim 1, wherein the substance is liquid, paste, or powder.

5. The method of manufacturing the portable container of claim 4, wherein the substance comprises medicine or cosmetics.

6. The method of manufacturing the portable container of claim 4, wherein the substance is liquid medicine comprising hydrogen peroxide solution, merbrom in solution, acrinol solution, methylrosaniline chloride solution, or providone solution.

7. The method of manufacturing the portable container of claim 4, wherein the substance is maintenance cosmetics comprising cleansing water, nail polish, or phytoncide.

8. The method of manufacturing the portable container of claim 4, wherein the substance is a chemical comprising casein glue, urea formaldehyde glue, phenol formaldehyde glue, formaldehyde resin glue, acid-vinyl acetate rubber, or nitrocellulose glue.

9. The method of manufacturing the portable container of claim 4, wherein the substance is powder drugs or cosmetics comprising a sulfa drug having anti-bacterial properties.

10. The method of manufacturing the portable container of claim 4, wherein the substance is kept in the receiving space by the negative pressure in the receiving space to avoid spraying.

11. The method of manufacturing the portable container of claim 10, wherein the substance is liquid medicine comprising hydrogen peroxide solution, merbrom in solution, acrinol solution, methylrosaniline chloride solution, or providone solution.

12. The method of manufacturing the portable container of claim 10, wherein the substance is maintenance cosmetics comprising cleansing water, nail polish, or phytoncide.

13. The method of manufacturing the portable container of claim 10, wherein the substance is a chemical comprising casein glue, urea formaldehyde glue, phenol formaldehyde glue, formaldehyde resin glue, acid-vinyl acetate rubber, or nitrocellulose glue.

14. The method of manufacturing the portable container of claim 10, wherein the substance is powder drugs or cosmetics comprising a sulfa drug having anti-bacterial properties.

* * * * *